United States Patent
Feng et al.

(10) Patent No.: US 8,700,421 B2
(45) Date of Patent: *Apr. 15, 2014

(54) INFUSION PUMP WITH CONFIGURABLE SCREEN SETTINGS

(75) Inventors: Wen Feng, San Diego, CA (US); John Arrizza, San Diego, CA (US); Mihaela Cozmi, Gilroy, CA (US); Glenn Davis, Grayslake, IL (US); Marwan A. Fathallah, Mundelein, IL (US); Angela Marino, Deerfield, IL (US); John Erik Michael Palmroos, San Diego, CA (US); James R. Shults, Ramona, CA (US); Suzanne Willey, San Diego, CA (US); Yu Xin, San Diego, CA (US)

(73) Assignee: Hospira, Inc., Lake Forest, IL (US)

( * ) Notice: Subject to any disclaimer, the term of this patent is extended or adjusted under 35 U.S.C. 154(b) by 590 days.

This patent is subject to a terminal disclaimer.

(21) Appl. No.: 12/337,200

(22) Filed: Dec. 17, 2008

(65) Prior Publication Data

US 2009/0153058 A1 Jun. 18, 2009

Related U.S. Application Data

(60) Provisional application No. 61/014,660, filed on Dec. 18, 2007.

(51) Int. Cl.
*G06Q 10/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | | |
|---|---|---|---|
| 3,901,231 A | 8/1975 | Olson | |
| 5,431,627 A | 7/1995 | Pastrone et al. | |
| 5,445,621 A | 8/1995 | Poli et al. | |
| 5,496,273 A | 3/1996 | Pastrone et al. | |
| 5,681,285 A | 10/1997 | Ford | |
| 5,685,844 A | 11/1997 | Marttila | |
| 5,687,717 A | 11/1997 | Halpern et al. | |
| 5,713,856 A | 2/1998 | Eggers | |
| 5,718,562 A | 2/1998 | Lawless et al. | |
| 5,764,034 A * | 6/1998 | Bowman et al. | 320/155 |
| 5,766,155 A | 6/1998 | Hyman | |
| 5,772,635 A | 6/1998 | Dastur et al. | |
| 5,782,805 A | 7/1998 | Meinzer et al. | |
| 5,800,387 A | 9/1998 | Duffy et al. | |
| 5,814,015 A | 9/1998 | Gargano et al. | |
| 5,957,885 A | 9/1999 | Bollish et al. | |
| 6,269,340 B1 | 7/2001 | Ford | |
| 6,418,535 B1 | 7/2002 | Kulakowski et al. | |
| 6,468,242 B1 * | 10/2002 | Wilson et al. | 604/65 |
| 6,753,842 B1 | 6/2004 | Williams et al. | |
| 2002/0029776 A1 * | 3/2002 | Blomquist | 128/200.11 |
| 2002/0038392 A1 | 3/2002 | De La Huerga | |
| 2002/0077852 A1 | 6/2002 | Ford | |

(Continued)

*Primary Examiner* — Robert Morgan
*Assistant Examiner* — Rajiv Raj
(74) *Attorney, Agent, or Firm* — Michael R. Crabb

(57) ABSTRACT

A method and apparatus provides for configuring the backlight brightness level. The backlight brightness level can be configured at the drug library and/or at the medical device, thereby improving the flexibility a user has in changing backlight parameters. A method and apparatus for managing a power saving mode allows the user to configure the power saving program at the drug library and/or at the medical device.

12 Claims, 10 Drawing Sheets

(56) References Cited

U.S. PATENT DOCUMENTS

| | | |
|---|---|---|
| 2004/0128162 A1 | 7/2004 | Schlotterbeck |
| 2004/0152970 A1 | 8/2004 | Hunter et al. |
| 2005/0144043 A1 | 6/2005 | Holland et al. |
| 2005/0177096 A1 | 8/2005 | Bollish et al. |
| 2006/0100907 A1 | 5/2006 | Holland et al. |
| 2006/0116639 A1 | 6/2006 | Russell |
| 2006/0200369 A1 | 9/2006 | Batch |
| 2006/0229557 A1 | 10/2006 | Fathallah et al. |
| 2006/0258985 A1 | 11/2006 | Russell |
| 2006/0271286 A1 | 11/2006 | Rosenberg |
| 2007/0118405 A1 | 5/2007 | Campbell |
| 2007/0213598 A1 | 9/2007 | Howard et al. |
| 2007/0214003 A1 | 9/2007 | Holland et al. |
| 2008/0200870 A1 | 8/2008 | Palmroos et al. |
| 2008/0243055 A1 | 10/2008 | Fathallah et al. |

\* cited by examiner

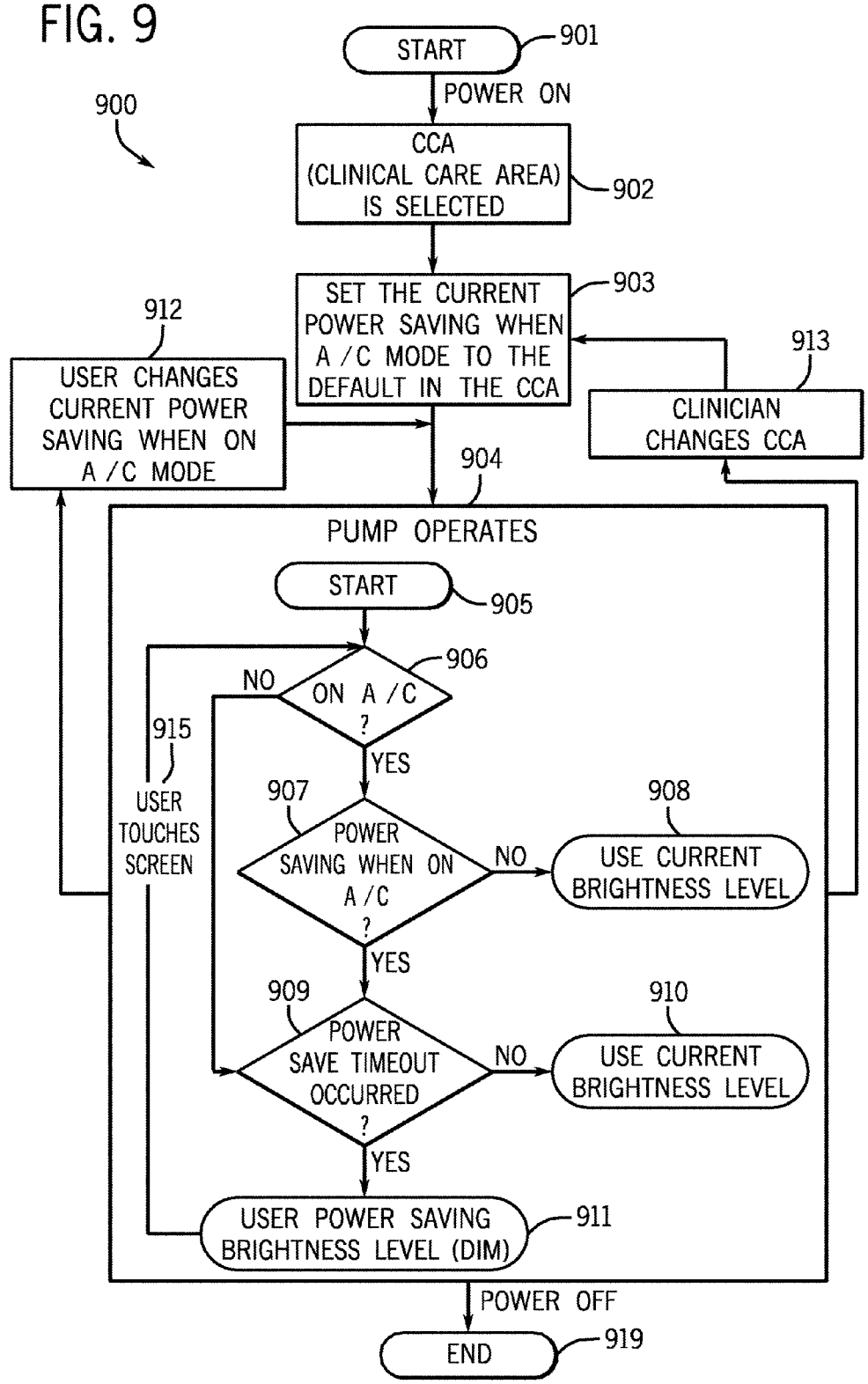

INFUSION PUMP WITH CONFIGURABLE SCREEN SETTINGS

CROSS REFERENCE TO RELATED APPLICATIONS

This application claims priority based upon U.S. Provisional Application Ser. No. 61/014,660 filed Dec. 18, 2008, which is expressly incorporated herein by reference in its entirety.

TECHNICAL FIELD

The present invention relates to medical devices. More specifically, the invention relates to infusion pumps that include touch screen graphical user interfaces.

BACKGROUND OF THE INVENTION

Modern medical devices, including medical pumps, can be complicated and time-consuming for caregivers to program. Human errors in pump programming and other medication errors can have adverse or even deadly consequences for the patient. The need for an improved graphical interface is critical to maintain efficiency of patient care and to reduce potential clinical errors and thereby improve patient safety. Device interfaces that increase input efficiency and accuracy are critical to improve patient safety and therapy.

One critical need for the patient caregiver is to have a graphical user interface or display that is easy to read. Many graphical user interfaces have a backlight to improve the visualization of the screen during programming and running of the infusion. One drawback for many of these devices is that the backlight is not adjustable. In these devices, the set level of brightness may be too high for clinical care areas that have patients that are sensitive to light, such as neonatal intensive care units. Conversely, the set level of brightness may be too low for areas that have a high level of ambient light such as an operating room or an emergency room.

Some devices may allow adjustment of the backlight brightness level. However, the procedure to adjust the brightness level to suit the user and/or the location is often time consuming and inconvenient, thereby reducing the efficiency of the caregiver.

Another drawback to graphical user interfaces that have backlights is that often the device has a power saving mode that dims the backlight after a predetermined length of time to conserve power and to prevent undue wear and tear on the display hardware. Often the predetermined time is a minute or two, requiring the user to continuously touch the device to brighten the backlight during procedures lasting more than a few minutes. This can be cumbersome and inefficient. Worse, it is distracting and disruptive to the clinical caregiver since it takes the user away from the task at hand and therefore could lead to patient harm.

Therefore, it would be desirable to have a medication management system and a medical device that overcomes these and other disadvantages.

To that end, it is an object of this invention to provide a device where the backlight is configurable based on the clinical care area where the infusion will take place and/or user preferences.

It is another object of this invention to provide a device where the power saving mode is configurable based on the clinical care area.

It is a further object of the invention to provide a method of adjusting the backlight brightness level that is efficient for the user.

SUMMARY OF THE INVENTION

A method and apparatus is disclosed for configuring the backlight brightness level. The backlight brightness level can be configured at the drug library and/or at the medical device, thereby improving the flexibility a user has in changing backlight parameters.

Another aspect of the present invention provides a method and apparatus that allows the user to configure a power saving option or program at the drug library and/or at the medical device.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 9 is a flow chart for a program for setting a power saving mode, in accordance with the present invention.

DETAILED DESCRIPTION OF THE PRESENTLY PREFERRED EMBODIMENTS

Figure 1:
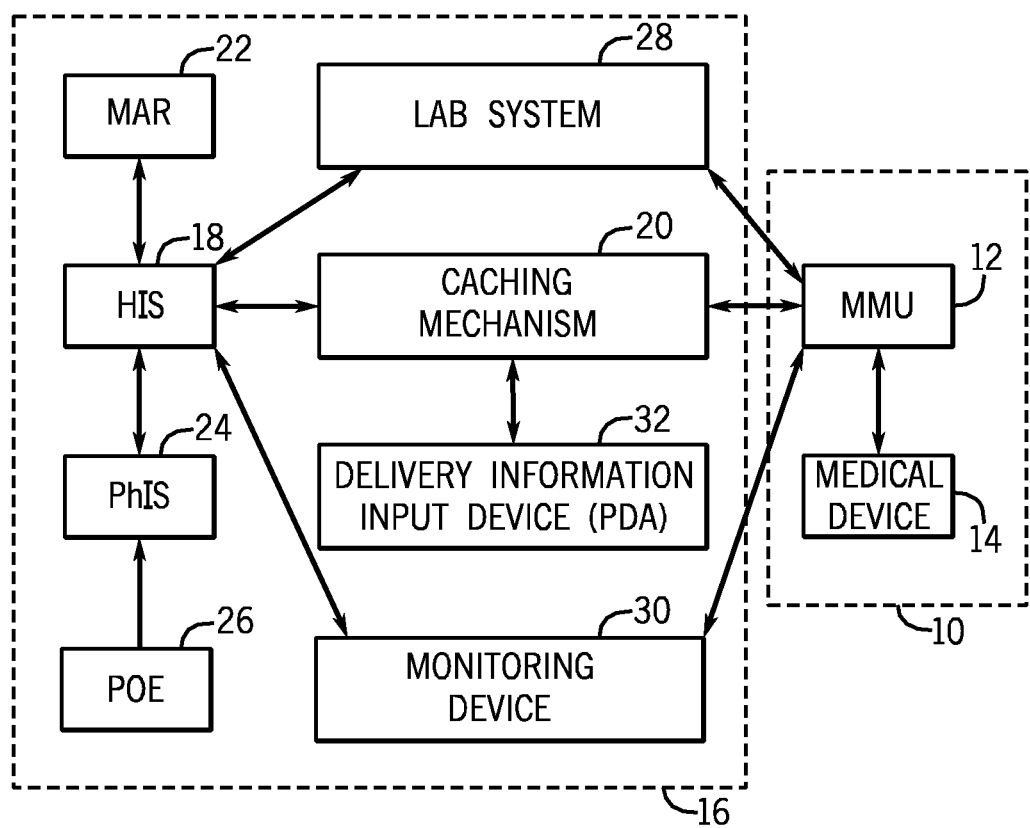
FIG. 1 is a schematic diagram of the medication management system including a medication management unit and a medical device, integrated with an information system, in accordance with the present invention.

The present invention will be described as it applies to its preferred embodiment. It is not intended that the present invention be limited to the preferred embodiment. It is intended that the invention cover all modifications and alternatives that may be included within the scope of the appended claims With reference to FIG. 1, the medication management system (MMS) 10 of the present invention includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. As discussed below, there can be a variety of information systems in a hospital environment. As shown in FIG. 1, the MMU 12 communicates to a hospital information system (HIS) 18 via a caching mechanism 20 that is part of the hospital environment 16.

It will be understood by those of skill in art that the caching mechanism 20 is primarily a pass through device for facilitating communication with the HIS 18 and its functions can be eliminated or incorporated into the MMU 12 (FIG. 1) and/or the medical device 14 and/or the HIS 18 and/or other information systems or components within the hospital environment 16. The caching mechanism 20 provides temporary storage of hospital information data separate from the HIS 18, the medication administration record system (MAR) 22, pharmacy information system (PhIS) 24, physician order entry (POE) 26, and/or Lab System 28. The caching mechanism 20 provides information storage accessible to the Medication Management System 10 to support scenarios where direct access to data within the hospital environment 16 is not available or not desired. For example, the caching mechanism 20 provides continued flow of information in and out of the MMU 12 in instances where the HIS 18 is down or the connectivity between the MMU 12 and the electronic network (not shown) is down.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. As shown, the MMU 12 communicates directly to the lab system 28 and monitoring device 30. However, it will be understood to those of skill in art that the MMU 12 can communicate to the lab system 28 and monitoring device 30 indirectly via the HIS 18, the caching mechanism 20, the medical device 14 or some other intermediary device or system.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
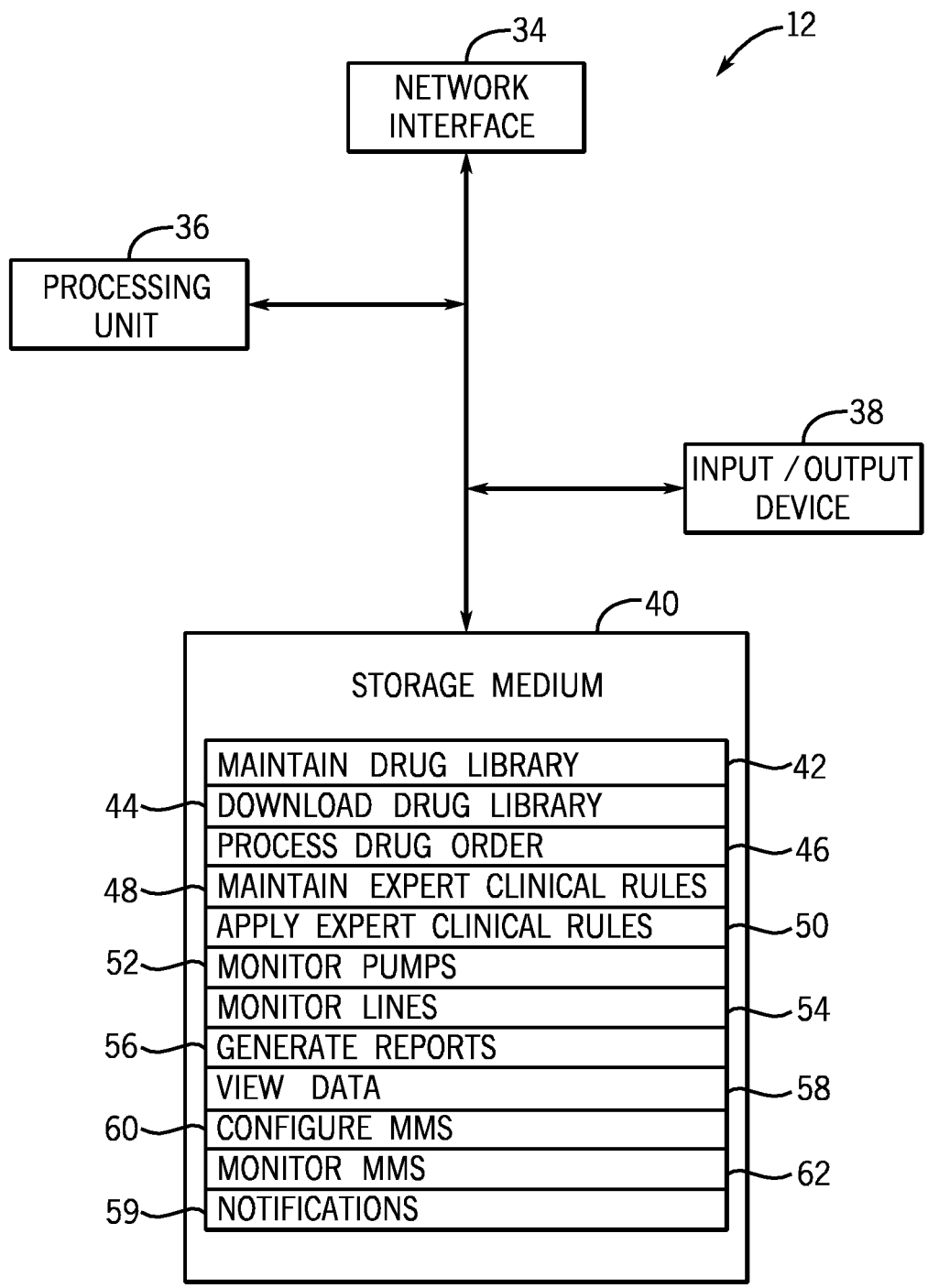
FIG. 2 is a schematic diagram of the medication management unit, in accordance with the present invention.

With reference to FIG. 2, the medication management unit 12 includes a network interface 34 for connecting the MMU 12 to multiple components of a hospital environment 16, one or more medical devices 14, and any other desired device or network. A processing unit 36 is included in MMU 12 and performs various operations described in greater detail below. A display/input device 38 communicates with the processing unit 36 and allows the user to receive output from processing unit 36 and/or input information into the processing unit 36. Those of ordinary skill in the art will appreciate that display/input device 38 may be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed in accordance with the present invention for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions. The Monitor Pumps 52 program acquires ongoing updates of status, events, and alarms transmitted both real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS 10 components and processing, and other aspects of day-to-day operations such as system start up, shut down, backup and restore.

Figure 3:
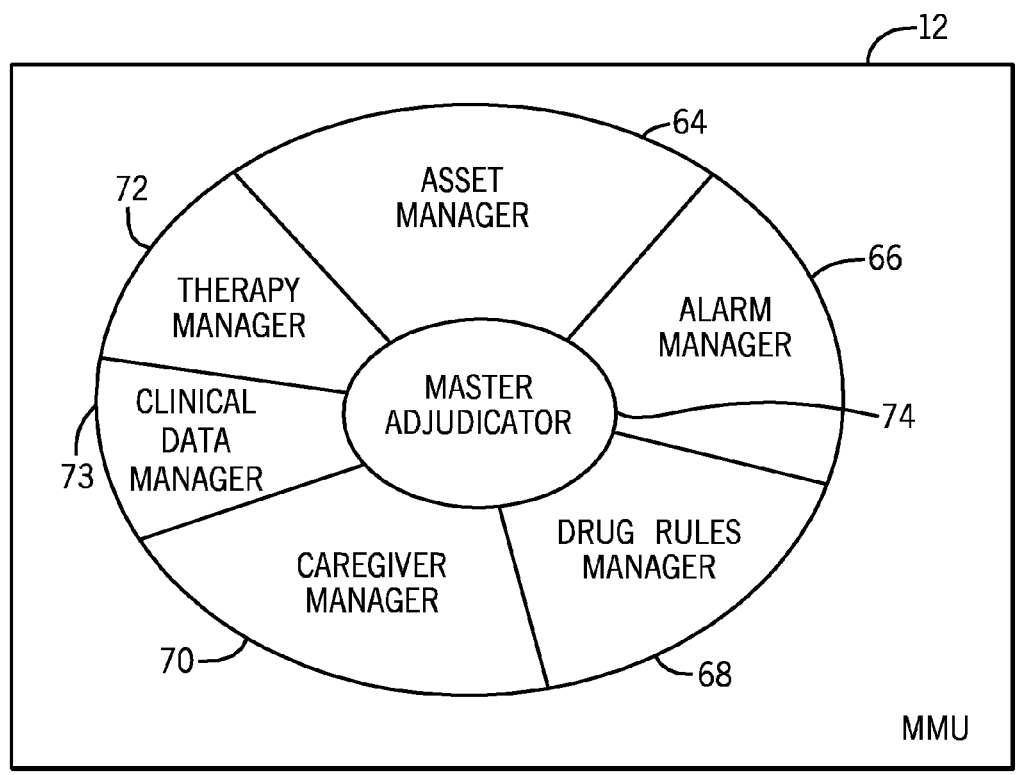
FIG. 3 is a schematic diagram illustrating some of the major functions performed by the medication management unit, in accordance with the present invention.

With reference to FIG. 3, the various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, is included in HOSPIRA MEDNET software) 68, a caregiver manager 70, a therapy manager 72, and/or a clinical data manager 73. However, one of ordinary skill in the art will appreciate that additional or alternative hospital system managing units can be provided without departing from the present invention. Additionally, the MMU 12 includes a master adjudicator 74 between the separate interrelated hospital system managing units 64-73 of the MMU 12, to regulate the interaction between the separate management units.

Further, while the MMU 12 as described herein appears as a single device, there may be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 74 assigns redirected service requests to another server portion of the MMU 12, prioritizing each request and also ensuring that each request is processed.

With reference to FIGS. 2 and 3, the managing units 64-72 each include separate features and rules to govern their operation. For example, the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the hospital system managing units 64-73 can be made in accordance with the present invention.

Figure 4:
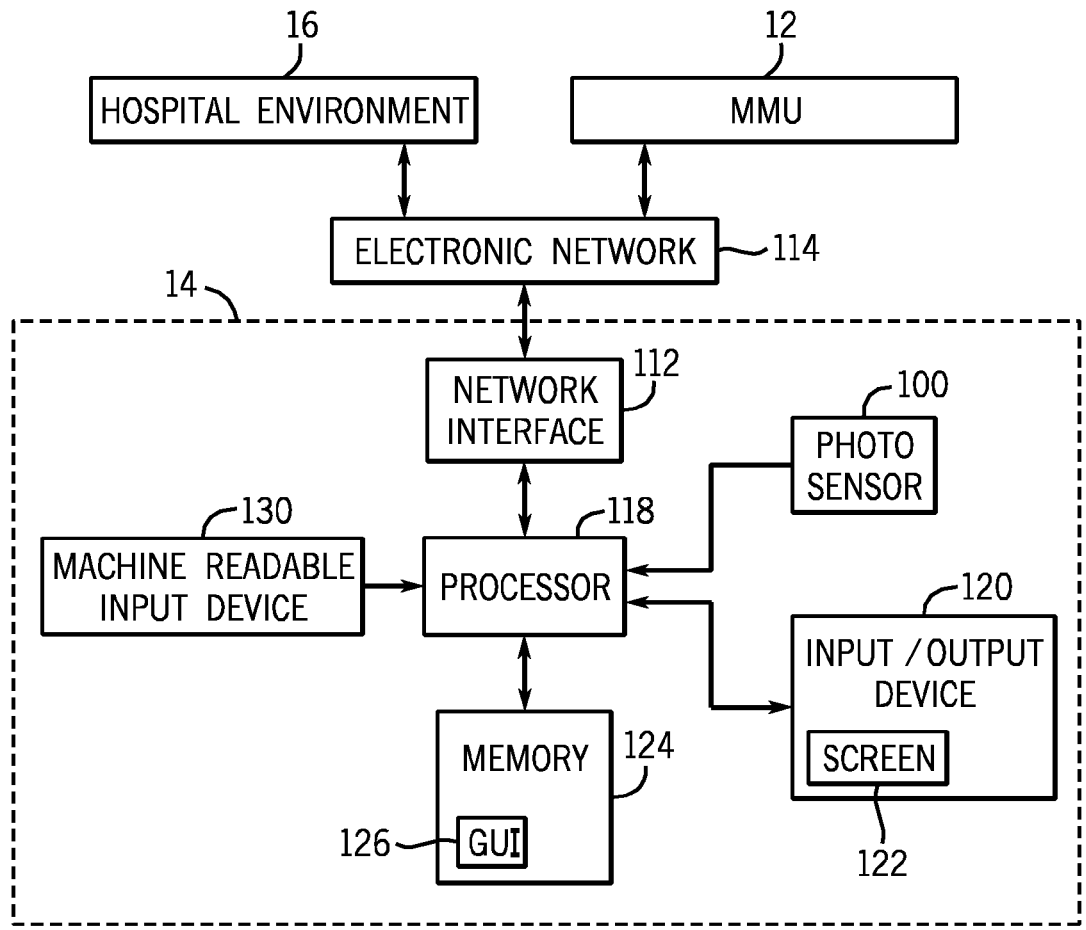
FIG. 4 is a schematic diagram of a medical device, in accordance with the present invention.

With reference to FIG. 4, an electronic network 114 connects the MMU 12, medical device 14, and hospital environment 16 for electronic communication. The electronic network 114 can be a completely wireless network, a completely hard wired network, or some combination thereof.

FIG. 4 is a schematic diagram illustrating several functional components of a medical device 14 for implementing the present invention. Those of ordinary skill in the art will appreciate that the device 14 includes many more components than those shown in FIG. 4. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic, testing or sampling device.

Figure 5:
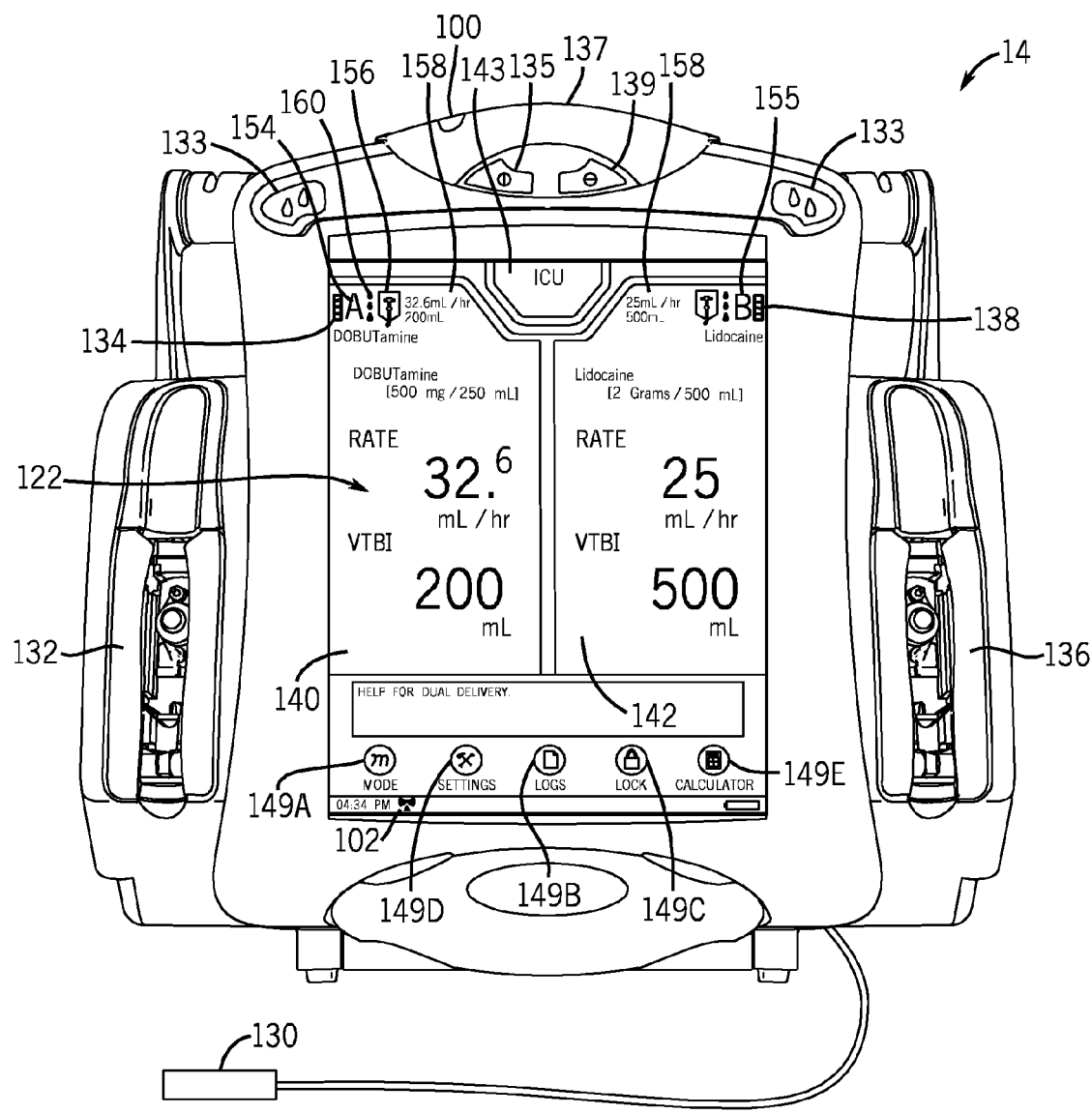
FIG. 5 is perspective view of a multi-channel medical device in communication with a machine-readable input device according to the present invention and shows a split screen display, having one portion associated with each channel, which is adapted to be displayed and viewed from afar during normal delivery of fluid, in accordance with the present invention.

With reference to FIG. 5, for the purpose of exemplary illustration only, the medical device 14 is disclosed as an infusion pump. More particularly, the medical device 14 can be a single channel infusion pump, a multi-channel infusion pump (as shown), or some combination thereof.

With reference to FIG. 4, the pump style medical device 14 includes a network interface 112 for connecting the medical device 14 to electronic network 114. Where a wireless connection to the electronic network 114 is desired, network interface 112 operates an antenna for wireless connection to the electronic network 114. The antenna can project outside the device 14 or be enclosed within the housing of the device.

A processor 118 is included in the medical device 14 and performs various operations described in greater detail below. The input/output device 120 allows the user to receive output from the medical device 14 and/or input information into the medical device 14. Those of ordinary skill in the art will appreciate that input/output device 120 may be provided as a single device such as a touch screen 122, or as a separate display device and a separate input device (not shown). In the preferred embodiment, the display screen 122 of the medical pump 14 is a thin film transistor active matrix color liquid crystal display with a multi-wire touch screen. A membrane generally impermeable to fluids overlays the display screen 122 so the user can press on images of keys or buttons on the underlying screen with wet gloves, dry gloves or without gloves to trigger an input.

A memory 124 communicates with the processor 118 and stores code and data necessary for the processor 118 to perform the functions of the medical device 14. More specifically, the memory 124 stores multiple programs formed in accordance with the present invention for various functions of the medical device 14 including a graphical user interface program 126 with multiple subparts described in greater detail below.

With reference to FIG. 5, the present invention provides a machine-readable input device 130. The machine-readable input device 130 communicates with the medical device 14 to input machine-readable information to the medical device 14. The machine-readable input device 130 can communicate, directly or indirectly, with the medical device 14 via a wireless or hard-wired connection. The machine-readable input device 130 can be a device that is separate from but associated or in communication with the medical device 14. The machine-readable input device 130 can be any sort of data input means, including those adapted to read machine-readable indicia, such as a barcode scanner or handheld personal digital assistant (PDA). Alternatively, the machine-readable input device 130 may be operable to read in other known forms of machine-readable information, such as radio frequency identification tags (RFID), touch memory, digital photography, biometrics, etc.

With reference to FIG. 5, the medical device 14 is a multi-channel pump having a first channel 132 with first channel machine-readable label 134 and a second channel 136 with a second channel machine-readable label 138. A user of the medical device 14 operates the machine-readable input device 130 to select a channel from one or more channels 132 and 136, by scanning in the associated machine-readable label 134 or 138.

The user selects the desired channel 132 or 136 by using the machine-readable input device 130 to scan a factory or hospital programmed, unique, machine-readable label 134 or 138 that is electronically generated and presented on the screen 122, preferably juxtapositioned near the respective channel 132 or 136. Alternatively, the machine-readable labels 134 and 138 are physically affixed to the medical device 14, preferably on or juxtapositioned near the channel 132 and 136, respectively. Since the machine-readable labels 134 and 138 are generated and/or can be stored in memory 124 by the pump 14, the pump 14 can associate the machine-readable labels 134 and 138 to the channels 132 or 136. The pump 14 then allows the user to program and activate the selected channel 132 or 136. The user may also manually select the desired channel by touching an appropriate folder tab on the touch screen. The folder tabs are labeled and/or physically arranged on the screen so as to be proximate to the corresponding channel 132 or 136.

In a further aspect of the wireless embodiment, all the medical devices can periodically broadcast a unique wireless device/channel IP address and/or a self-generated unique machine-readable label (for example, a barcode) 134 or 138 that can also be presented on the screen 122. Alternatively, the machine-readable labels 134 and 138 are physically affixed to or posted on the medical device 14. Each medical device will correlate such broadcasted or posted device/channel IP addresses and/or barcodes with a particular patient, who is also identified by a unique machine readable label (not shown) or patient IP address. The user associates the desired pump(s) or channel(s) 132, 136 with the patient by using the machine-readable input device 130 to scan the unique machine-readable labels 134, 138 and the patient's machine readable label. This causes the appropriate pump processor(s) 118 to associate the appropriate pump channel(s) 132, 136 with the patient. Then the pumps or channels can associate, communicate, and coordinate with each other wirelessly.

With reference to FIGS. 4 and 5, the graphical user interface program 126 reallocates screen 122 for a medical device 14. Specifically, FIG. 5 illustrates a multi-channel infusion pump 14 with a split touch screen 122 having a first channel screen portion 140 associated with first channel 132 and a second channel screen portion 142 associated with the second channel 136. Each channel screen portion 140 and 142 presents a subset of the delivery information regarding the respective channels 132 or 136, including without limitation therapeutic agent name, concentration, dose rate, VTBI, and alarm information, in a font size that it is easily readable by a user from a distance such as, for example, from approximately fifteen to twenty feet (4.6-6.2 meters) away. This is what is referred to as a "far view" delivery screen. The far view delivery screens display subsets of the information found on the relevant "near view" delivery screens. The near view delivery screen displays drug name, concentration, dose rate, time remaining, VTBI, volume remaining, and alarm name for the highest priority alarm if in an alarm state. The near view delivery screen will switch to the far view delivery screen after a defined period of time that is predetermined by the manufacturer, configurable by the facility via the drug library, and/or set by the caregiver at the pump, for example after 20 seconds.

Upon a user touching one of the tabs "A" or "B" or anywhere on the channel screen portions 140 or 142 of the far view delivery screen, a "near view" delivery screen is presented on the screen 122. The channel screen portion 140 or 142 selected or corresponding to the tab selected expands in area but the size of at least some of the text therein is shrunk.

The shrinkage of one of the channel screen portions 140 and 142 and enlargement of its counterpart provides additional space for one or more data display or data entry fields to be placed on screen 122. As discussed below, data displays or data entry fields are placed on screen 122 in space previously occupied by portions of the channel screen portion 140 or 142. This reallocation of space on screen 122 permits the user to enter inputs more easily since the data entry field can be large, preferably at least as large or, more preferably, larger in area than the original channel screen portions 140 and 142 were in the delivery screen mode. Additionally, the reallocation of space on screen 122 provides greater space for presenting information on the channel being adjusted or monitored. Further details on the reallocation of screen 122 and the near view and far view delivery screens can be found in commonly owned and co-pending application U.S. Ser. No. 11/103,235 entitled USER INTERFACE IMPROVEMENTS FOR MEDICAL DEVICES filed on Apr. 11, 2005, which is expressly incorporated herein in its entirety.

Referring again to FIG. 5, pump 14 includes dedicated or fixed tactile infuser buttons, and images of buttons on the LCD-touch screen 122. The fixed tactile buttons 133, 135, 137, and 139 provide the following functions: LOAD/EJECT button 133—opens and closes the cassette carriage; ON/OFF button 135—turns power on and off; ALARM SILENCE button 137—silences a silenceable alarm for a specified period of time, for example two minutes; and EMERGENCY STOP button 139—stops all channels.

The LCD color touch screen 122 allows the user to access and use on-screen button images, for example 3D button images, and data entry fields. The touch screen 122 uses a membrane over the LCD display so a single keypress does not cause significant infusion pole movement nor is it mistaken for a double keypress. The touch screen also accommodates a keypress whether the user is wearing wet gloves, dry gloves, or no gloves.

Figure 5A:
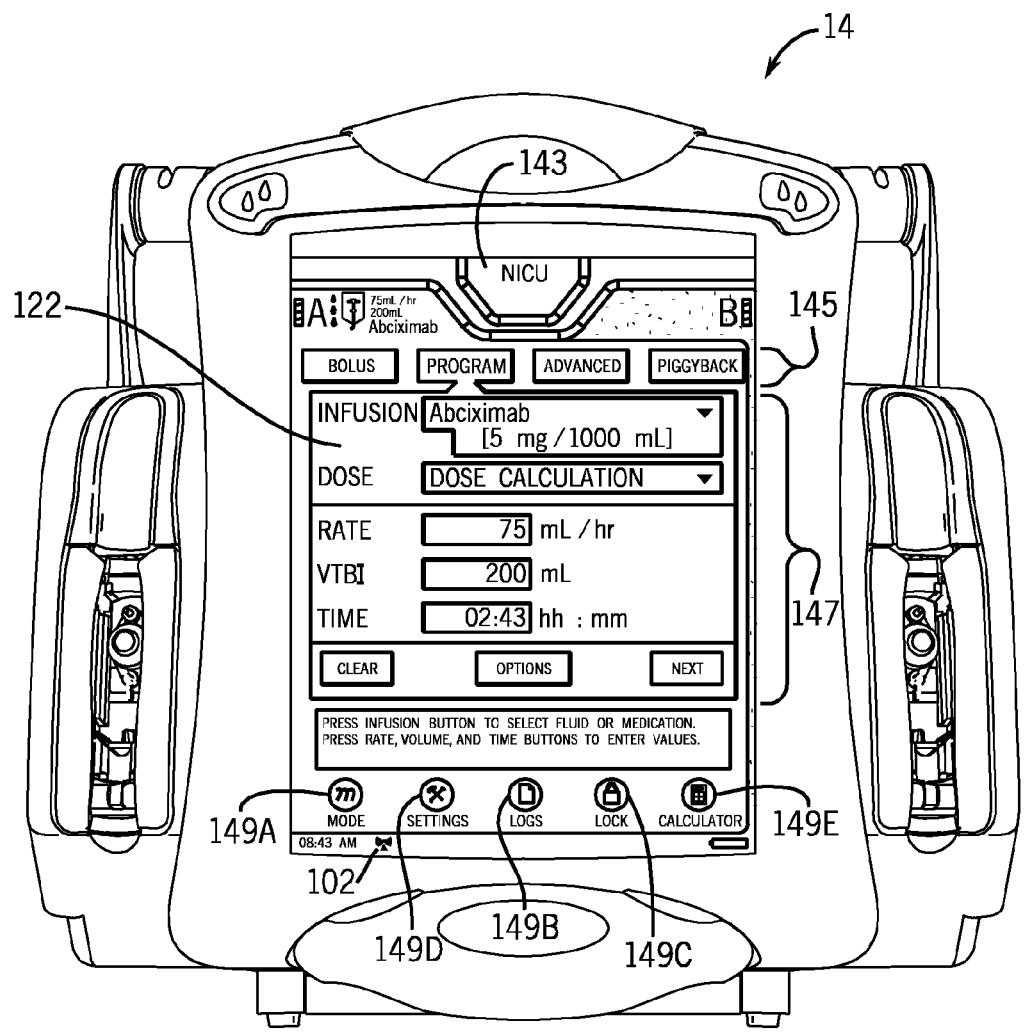
FIG. 5A is a perspective view similar to FIG. 5 and illustrates a near view display screen, in accordance with the present invention.

LCD touch screen button images 143, 145, 147 and 149A-149E are located as shown in FIGS. 5 and 5A and perform the following functions: Patient Information Tab 143—displays the clinical care area, preselected patient information (including without limitation name, ID number, etc.), and provides access to a more detailed patient information screen (not shown); Channel Level Therapy Buttons 145—accessed by button images on the infuser touch screen, are used to select an infusion therapy; Program Level Buttons 147—accessed by pressing areas, drop-down list triangles, boxes or text boxes on the programming screen, are used to select dose parameters of an infusion; and Device Level Buttons 149A-149E at the bottom of the touch screen are used to display and control device level features, including without limitation Mode 149A (for example, Operational or Biomed), Logs 149B, Lock 149C, Settings 149D, and Calculator display 149E. A wireless indicator image 102 displayed at the bottom of the screen 122 indicates that the device 14 is connected and ready for communication.

By using the Channel Level Therapy Buttons 145 and the Program Level Buttons 147, the healthcare practitioner can program each individual channel of the pump with specific fluid therapies in a variety of weight- and body surface area-based units such as micrograms/kg/hour, grams/m$^2$/hr, and other delivery specifications for the following modes: Basic Therapy—includes dose calculation, which allows dose rate programming based on volume to be infused (VTBI), drug amount, infusion time and drug concentration and simple rate programming that allows programming of volumetric rate (mL/hr) based upon VTBI and time; Bolus delivery—allows user to program a single uninterrupted discrete delivery based on dose amount and time (the bolus can be delivered from the primary or a secondary container); Piggyback delivery—allows user to program the delivery of a secondary infusion, to be delivered through the same cassette as the primary infusion (the primary infusion is paused until the piggyback VTBI completes); and Advanced Programming. Advanced Programming mode provides various types of programs including: Multistep—which allows a sequential delivery of fluid in up to 10 steps, with fluid volumes and delivery rates programmable for each step based on Rate and Volume or Volume and Time; Variable Time—which allows up to 24 dose calculation steps at specified clock times; Intermittent—a calculated dose or step to be delivered at regular intervals; and Taper—a delivery that ramps up and/or ramps down to a plateau rate.

With reference to FIGS. 4 and 5, the graphical user interface 126 provides channel indicators presented on screen 122. The channel indicators associate on-screen programming, delivery, and alarm information with a particular delivery channel by using graphical depictions such as a channel indication icon 154, 155. The channel indication icon 154 or 155 is a graphical item clearly associating on-screen programming, delivery, and alarm information with a specified associated delivery channel. The channel indication icons 154 and 155 are located on a tab 158 associated with a specified delivery channel of the medical device The channel indication icon 154 or 155 may include but is not limited to a user readable letter or number, a machine-readable indicator 134, or a combination thereof. The graphical user interface program 126 also provides a drip indicator icon 160 and an infusion status icon 156 presented on screen 122.

Medical device 14 is designed as a multi-processor, where many features are not hardwired, but instead can be uniquely configured based on rules, the location of the medical device 14, etc. In one embodiment, the features of the medical device are configured through the maintain drug library program 42 located within the storage medium 40 of MMU 12 (FIG. 2). The drug library is downloaded to the medical device 14 by the MMU 12. In another or the same embodiment, features of the medical device are configured at the medical device 14, which in this example is a pump 14.

FIGS. 6-9, illustrate the various embodiments for configuring a backlight feature of a medical device 14 through changes to the drug library (FIG. 6) and through changes at the pump (FIG. 7) in accordance with the present invention.

The drug library includes drug and device related information, which may include but is not limited to drug name, drug class, drug concentration, drug amount, drug units, diluent amount, diluent units, dosing units, delivery dose or rate, medication parameters or limits, device/infuser settings and/or modes, Clinical Care Area (CCA) designations and constraints, and library version. Through the maintain drug library program 42 the drug library may be configured to provide a medical device 14 that includes a customized display. In one embodiment, the display is customized based on the Clinical Care Area (CCA) the medical device 14 is located in, assigned to, and/or to be assigned to.

Figure 6:
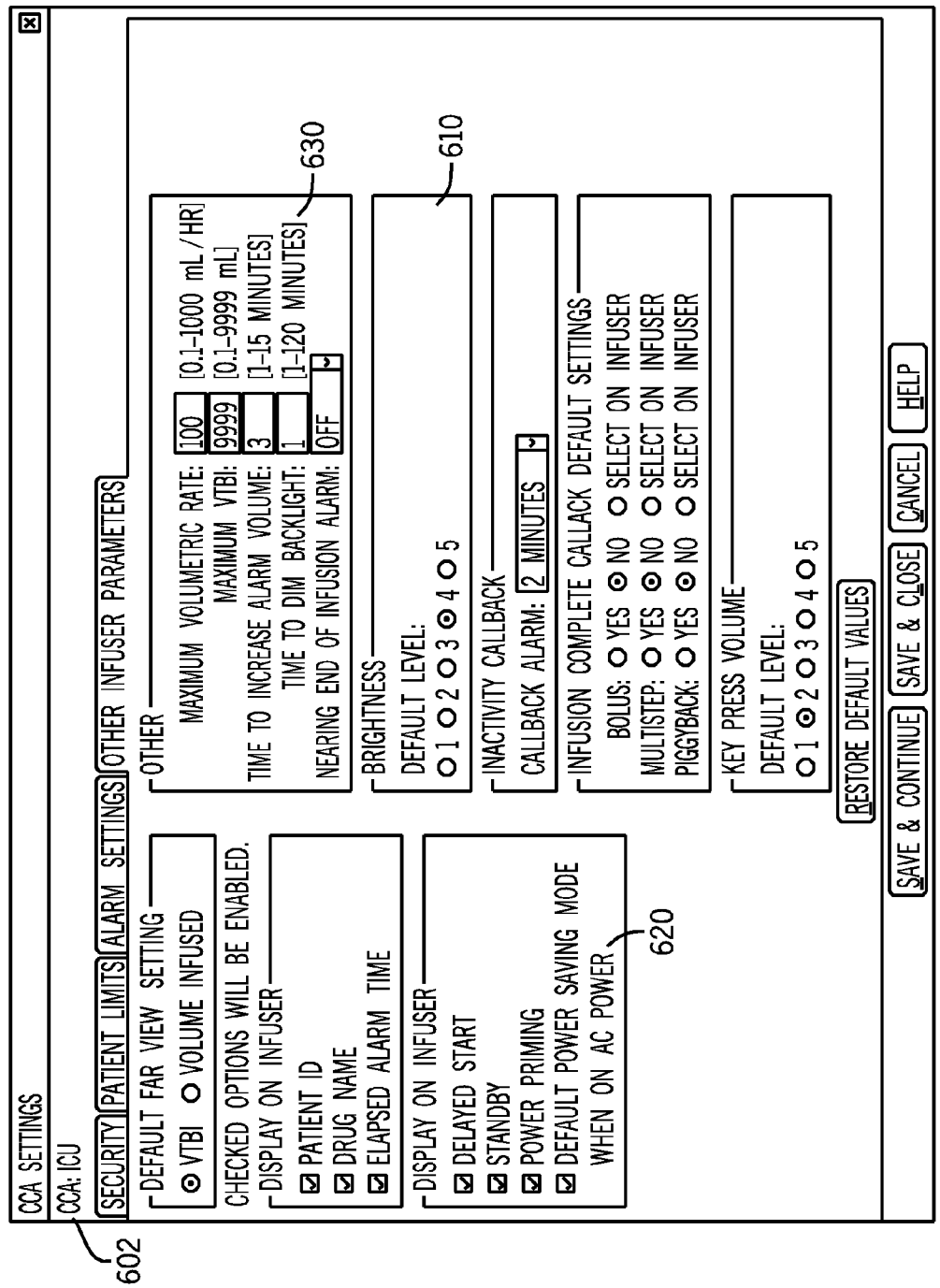
FIG. 6 is a screen shot of a graphical user interface for configuring CCA specific parameters, in accordance with the present invention.

FIG. 6 illustrates a graphical user interface 600 of an input device 38 within MMU 12 that is used to configure, within a drug library, a variety of device settings or parameters for a Clinical Care Area. In this example, the CCA is the Intensive Care Unit (ICU) 602, though it should be understood that device settings or parameters for other CCAs may be similarly configured. Pursuant to the present invention, graphical user interface 600 is used by authorized personnel, including but not limited to biomedical engineers, pharmacists, and nurses, to configure features relating to the backlight display. These features are, default brightness level 610, default power savings mode when on A/C power 620 and time to dim backlight 630. In the context used herein, the term brightness should be understood as including but not limited to contrast, backlighting, illumination output, and power consumption.

The default brightness level 610 is preset to a particular brightness level based on the CCA in which the medical device 14 resides. As illustrated, the default brightness level may be set from level 1 to level 5, with level 1 indicating the dimmest setting and level 5 indicating the brightest setting. Those with skill in the art will appreciate that the range of levels may be different than that illustrated, without departing from the scope of the present invention. As shown, a level 4 default brightness level has been selected for the ICU. The default brightness level may be lower or higher depending on the CCA where the medical device 14 resides. For example, in a neonatal ICU (NICU) the default brightness level may be set at level 1 or level 2 due to the light sensitivity of the neonates. Conversely, the default brightness level may be set at level 5 for medical devices that reside in an operating room (OR) or emergency room. In one embodiment, when a default brightness level has been selected for a particular medical device 14, the medical device 14 will maintain that default brightness level unless or until it is adjusted by a user/clinician at the device or is automatically dimmed, as will be discussed in detail below. If the default brightness level has been changed, the adjusted brightness level will revert to the default brightness level when the medical device 14 is turned off or when a new patient is indicated and the CCA is unchanged.

Figure 7:
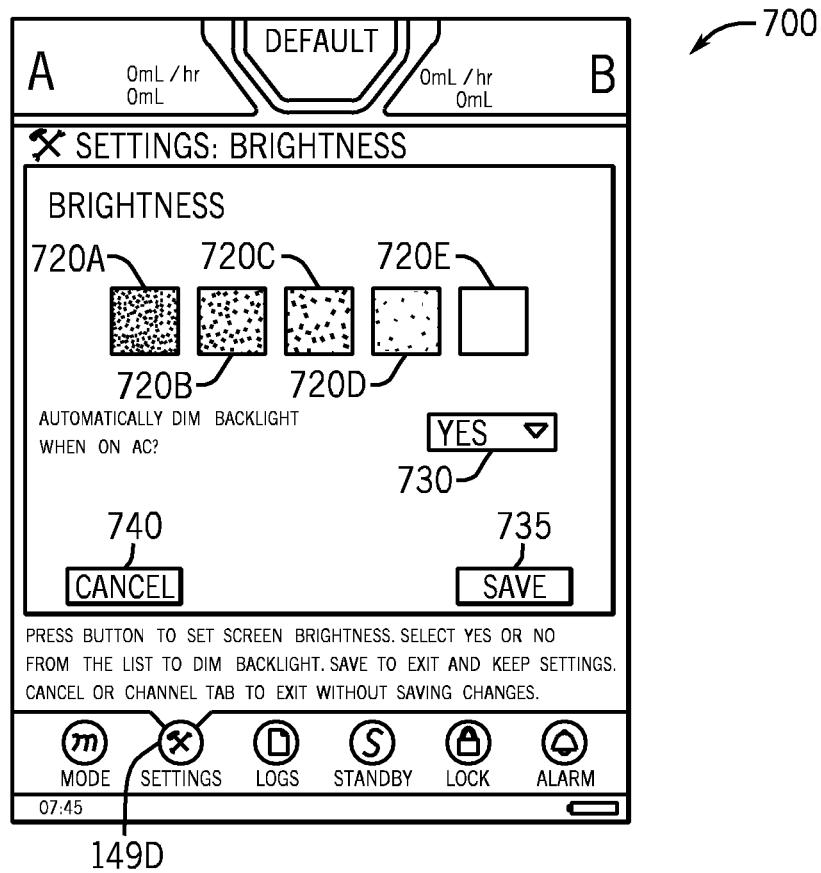
FIG. 7 is a screen shot of a graphical user interface for configuring medical device specific parameters, in accordance with the present invention.
Figure 8:
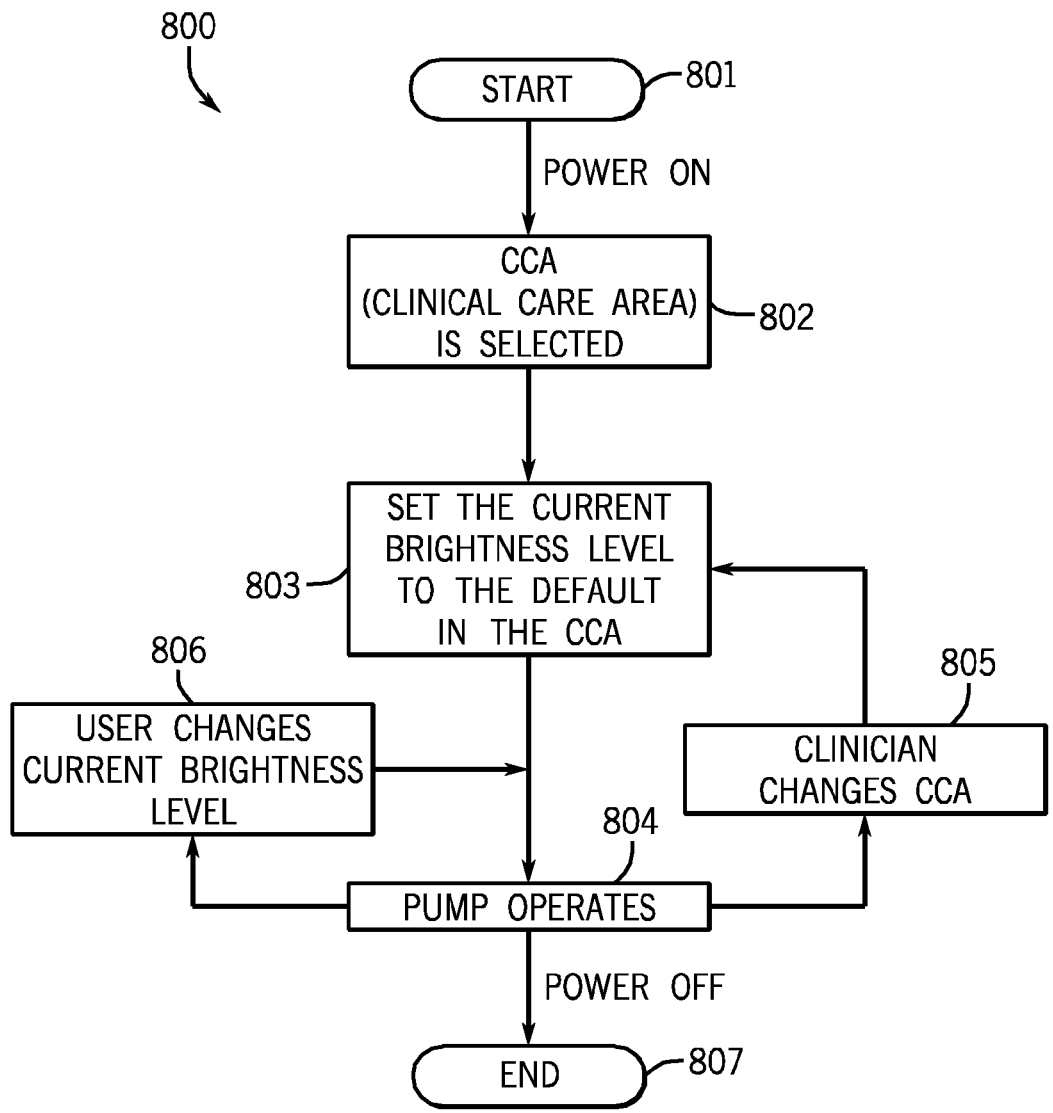
FIG. 8 is a flow chart for a program for setting display screen brightness level, in accordance with the present invention.

Referring now to FIG. 7, illustrated is a screen 700 of the multi-channel medical device of FIG. 5. In one embodiment of the present invention, a clinician may configure the brightness level of the display screen 122 at the medical device 14. In practice, to configure the brightness level, the clinician first presses the settings button 149D. Pressing the settings buttons 149D presents the clinician with a list of at least one configurable parameter (not shown). This list includes the configurable brightness setting that, when chosen via pressing a button or choosing the list from a drop down menu will access screen 700. Once at screen 700, the clinician sets the desired brightness level by pressing one of the brightness buttons 720A to 720E. Buttons 720A to 720E may be coded by color, brightness, shading or other indicators to indicate the level of brightness. In one embodiment, buttons 720A to 720E are progressively lighter in color from left to right to indicate the relative brightness level. In an example, button 720A is black to indicate the dimmest brightness level and button 720E is white to indicate the brightest level, with those buttons in between, 720B, 720C 720D, a gradient from dark gray to light gray. Once a button (720A to 720E) is pressed, the clinician confirms the chosen level by pressing the save button 735. The clinician can cancel the choice by pressing the cancel button 740. Pressing the save button 735 or the cancel button 740 exits the screen 700.

In one embodiment, a clinician can override the default brightness level 610 established via the drug library (FIG. 6) by configuring the brightness level at the medical device 14 on screen 700. In one embodiment, the clinician can override the default level to choose a level that is dimmer or brighter than the default level set at 610. In another embodiment, the clinician is limited to choosing a brightness level at screen 700 that is greater than the default level. This embodiment is useful when the medical device resides in the OR or ICU where ambient light is very bright. In another embodiment, the clinician is limited to choosing a brightness level at screen 700 that is less than the default level. This embodiment is particularly useful when the medical device resides in the NICU where the ambient light is maintained at a lower level for light sensitive patients.

With reference to FIGS. 1, 6, 7 and 8, a backlight brightness determination program 800 begins at 801 and proceeds to block 802 where, after the power to the pump is turned on, the clinician selects a CCA. Once the CCA is selected, at block 803, program 800 sets the medical device to the screen brightness default level 610 established in the drug library. At block 804, the medical device/pump is operated. During operation of the pump, as shown by block 806, a clinician may change the current brightness level at display screen 700, choosing and then confirming a new brightness level 720A to 720E.

The program 800 continues to operate the pump at block 804. Alternatively, during the operation of the pump at block 804, a clinician changes the CCA at block 805. Once the CCA is changed at block 805 the program 800 returns to block 803 where the current brightness level is set to the default level defined in the drug library for the new CCA. Program 800 ends at block 807.

Returning to FIG. 6, the backlight may be configured at 630 to dim after a predetermined length of inactivity of the clinician at the medical device 14. In the embodiment illustrated in FIG. 6, a user may set the time to dim backlight from 1 to 120 minutes after the last activity by the user. Those with skill in the art will appreciate that the time to dim backlight range may be other than the 1-120 minutes illustrated such as, for example, 1-240 minutes. In one embodiment, the range of time for time to dim backlight 630 may be determined based on the CCA in which the medical device will reside. In an example, the range for the time to dim backlight may be from 1-10 minutes for those medical devices 14 residing in CCAs having patients sensitive to light. In another example, the range for the time to dim backlight may be from 1 hour to 4 hours or more for those medical devices 14 residing in CCAs where a bright backlight without frequent dimming is critical such as the operating room.

FIG. 6 further illustrates that at graphical user interface 600 a user may configure the backlight using a default power saving mode when on A/C power 620 setting. To conserve power and wear and tear on the display hardware, some prior art devices have an automatic dimming feature that dims the display to a preset brightness level after a period set in the medical device. To restore the brightness level, the clinician must touch the display. In many situations, this is inefficient for the clinician, especially where the preset time to dim is very short. In accordance with the present invention, the power saving dimming feature may be turned on or off depending on such factors as, for example, the CCA in which the medical device currently resides, the CCA for which the medical device is being prepared for use, or the personal preference of the clinician. For example, where it is critical to the caregiver or the patient that the clinician not be distracted by having to return a display screen to an appropriate brightness by touching the screen, the power saving Default power saving mode when on A/C 620 may be turned off (i.e. not selected at 620). In other CCAs where dimming of the backlight is not as critical or is not critical, the Default power saving mode when on A/C may be selected at 620, as illustrated in FIG. 6 so that all medical devices within that CCA will dim after a preselected time.

In another embodiment illustrated in FIG. 7, the automatic power saving dimming feature may be configured as a setting at the pump by the user at 730. As shown at screen 700, the clinician may choose to automatically dim backlight when on A/C by choosing "Yes" at 730. Conversely, the clinician may turn off the automatic dimming feature by choosing "No" from the drop down menu.

With reference to FIGS. 1, 6, 7 and 9, a power saving when on A/C program 900 begins at block 901 and proceeds to block 902 where a CCA is selected by the clinician. Once the CCA is selected, program 900 sets the current power saving when on A/C mode to the default in the CCA, at block 903. Program 900 proceeds to block 904 where the medical device/pump 14 is operated. After pump 14 is started at block 905, program 900 determines at block 906 whether the pump is running on A/C power. If "yes", program 900 determines at block 907 whether the default has been set to the Power saving when on A/C mode. If yes, program 900 continues to block 909 to determine whether a power save timeout occurred. If yes, program 900 dims the pump backlight to the preset power saving brightness level at block 911. If no, program 900 proceeds to block 910 where the current brightness level is maintained. When at block 911 (from block 909), a clinician touches the dim display screen (block 915) and program 900 returns to block 906. At block 906, if it is determined that the pump is not on A/C then program 900 proceeds to block 909, otherwise program 900 returns to block 907. Alternatively at block 907, if it is determined that the power saving when on A/C was not set as the default at block 903 the current brightness level is maintained at block 908.

If, during the operation of pump 14 the user changes the current power savings when on A/C mode at screen 700, described above, program 900 returns in effect to block 906 where program 900 determines whether pump 14 is on A/C. If, during the operation of pump 14 the user changes the CCA at block 913, program 900 returns to block 903. Program 900 ends at block 919.

As will become apparent to one with skill in the art, the ability to configure these features 610, 620, 630, 720, 730 at the drug library and/or at the medical device 14 provides additional flexibility to the clinician and the hospital personnel that is unavailable in prior devices. One skilled in the art will appreciate from this disclosure that the functionality shown on screens 600 and 700 is made possible by computer program code, and as such those features could be combined, distributed or shared among the processors of the pump 14, the MMU 12, or other computers within the healthcare facility without detracting from the present invention. Those skilled in the art will also recognize from this disclosure that selecting the CCA and providing other information or input can be done via scanning or passively receiving input from drug containers, a patient identifier, a nurse identifier or other similar items.

While the embodiments of the invention disclosed herein are presently considered to be preferred, various changes and modifications can be made without departing from the scope of the invention. The scope of the invention is indicated in the appended claims, and all changes and modifications that come within the meaning and range of equivalents are intended to be embraced therein.

What is claimed is:

1. A method for configuring a backlight in a medical management system having a medication management unit and a medical device, the method comprising:
   at the medication management unit:
      receiving a selected clinical care area of a drug library;
      receiving a default power saving mode off/on setting for A/C powered medical device operation and a power save time out time limit for the selected clinical care area;
      updating the drug library with the default power saving mode off/on setting and the power save time out time limit; and
      transmitting the updated drug library;
   at the medical device in electronic communication with the medication management unit, the medical device having a display including the backlight, the medical device having both an A/C power mode and a non A/C power mode and being operable to run alternatively on one of A/C power in the A/C power mode and non A/C power in the non A/C power mode, the medical device further having a timed display dimming function responsive to the power save time out time limit:

receiving the updated drug library;

receiving a designated clinical care area selection that corresponds to the selected clinical care area from the updated drug library;

setting as a current power saving mode on/off setting for the designated clinical care area selection the default power saving mode on/off setting from the updated drug library; and operating the medical device in an A/C power mode in accordance with the current power saving mode on/off setting, enabling the timed display dimming function when the current power saving mode on/off setting is set to an on setting and disabling the timed display dimming function when the current power saving mode on/off setting is set to an off setting;

wherein the timed display dimming function, when enabled, is operable to dim the backlight to a preset power saving brightness level after the power save time out time limit, and the timed display dimming function, when disabled, is operable to maintain the backlight at a current brightness level.

2. The method of claim 1 wherein the operating the medical device in an A/C power mode in accordance with the current power saving mode on/off setting comprises the medical device:

determining an A/C power supply status at the medical device;

determining a current power saving mode status based on the determined A/C power supply status; and adjusting brightness level of the backlight based on the determined current power saving mode status.

3. The method of claim 1 wherein the operating the medical device in an A/C power mode in accordance with the current power saving mode on/off setting comprises the medical device:

determining an A/C power supply status at the medical device;

determining a current power saving mode status based on the determined A/C power supply status;

determining whether the power save time out time limit occurred; and adjusting brightness level of the backlight based on the determined power save time out time limit.

4. The method of claim 3 further comprising the medical device:

receiving user input seeking readjustment of the adjusted backlight brightness level; and readjusting the brightness level of the backlight based on the received user input.

5. The method of claim 1 further comprising the medical device:

receiving a current power saving mode on/off setting change; and adjusting the current power saving mode on/off setting based on the received current power saving mode on/off setting change.

6. The method of claim 1 further comprising the medical device:

receiving a designated clinical care area selection change; and adjusting the current power saving mode on/off setting based on the received designated clinical care area selection change.

7. A method for configuring a backlight in a medical management system having a medical device, the method comprising:

at the medical device having a display including the backlight, the medical device having both an A/C power mode and a non A/C power mode and being operable to run alternatively on one of A/C power in the A/C power mode and non A/C power in the non A/C power mode, the medical device further having a timed display dimming function responsive to the power save time out time limit:

receiving an updated drug library, the updated drug library having a default power saving mode off/on setting for A/C powered medical device operation and a power save time out time limit for a selected clinical care area;

receiving a designated clinical care area selection that corresponds to the selected clinical care area from the updated drug library;

determining the default power saving mode on/off setting for A/C powered medical device operation from the updated drug library for the designated clinical care area selection;

setting a current power saving mode on/off setting for the medical device in an A/C power mode as the determined default power saving mode on/off setting from the updated drug library for the designated clinical care area selection; and operating the medical device in an A/C power mode in accordance with the current power saving mode on/off setting thereby enabling the timed display dimming function when the current power saving mode on/off setting is set to an on setting and disabling the timed display dimming function when the current power saving mode on/off setting is set to an off setting;

wherein the timed display dimming function, when enabled, is operable to dim the backlight to a preset power saving brightness level after the power save time out time limit, and the timed display dimming function, when disabled, is operable to maintain the backlight at a current brightness level.

8. The method of claim 7 wherein the operating the medical device in an A/C power mode in accordance with the current power saving mode on/off setting comprises the medical device:

determining an A/C power supply status at the medical device;

determining a current power saving mode status based on the determined A/C power supply status; and adjusting brightness level of the backlight based on the determined current power saving mode status.

9. The method of claim 7 wherein the operating the medical device in an A/C power mode in accordance with the current power saving mode on/off setting comprises the medical device:

determining an A/C power supply status at the medical device;

determining a current power saving-mode status based on the determined A/C power supply status;

determining whether the power save time out time limit occurred; and adjusting brightness level of the backlight based on the determined power save time out time limit.

10. The method of claim 9 further comprising the medical device:

receiving user input seeking readjustment of the adjusted backlight brightness level; and readjusting the brightness level of the backlight based on the received user input.

11. The method of claim 7 further comprising the medical device:
- receiving a current power saving mode on/off setting change at the medical device; and
- adjusting the current power saving mode on/off setting based on the received current power saving mode on/off setting change.

12. The method of claim 7 further comprising the medical device:
- receiving a designated clinical care area selection change; and
- adjusting the current power saving mode on/off setting based on the received designated clinical care area selection change.

* * * * *